(12) United States Patent
Xi et al.

(10) Patent No.: US 12,022,813 B2
(45) Date of Patent: Jul. 2, 2024

(54) HOMOGENIZATION METHOD OF INFECTING A MOSQUITO WITH WOLBACHIA

(71) Applicant: Board of Trustees of Michigan State University, East Lansing, MI (US)

(72) Inventors: Zhiyong Xi, Okemos, MI (US); Meichun Zhang, Okemos, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 17/943,348

(22) Filed: Sep. 13, 2022

(65) Prior Publication Data

US 2024/0057573 A1 Feb. 22, 2024

Related U.S. Application Data

(60) Provisional application No. 63/398,259, filed on Aug. 16, 2022.

(51) Int. Cl.
*A01K 67/033* (2006.01)

(52) U.S. Cl.
CPC ...... *A01K 67/033* (2013.01); *A01K 2227/706* (2013.01); *A01K 2267/02* (2013.01)

(58) Field of Classification Search
CPC ............ A01K 67/033; A01K 2227/706; A01K 2267/02

See application file for complete search history.

(56) References Cited

U.S. PATENT DOCUMENTS

| 7,868,222 | B1 | 1/2011 | Dobson |
| 9,090,911 | B2 | 7/2015 | O'Neill et al. |
| 11,344,009 | B2 | 5/2022 | Hoang et al. |
| 2011/0145939 | A1 | 6/2011 | O'Neill |

FOREIGN PATENT DOCUMENTS

| CN | 102349473 B | 6/2013 |
| WO | WO-2006008652 A1 | 1/2006 |
| WO | WO-2012145145 A2 | 10/2012 |

OTHER PUBLICATIONS

Machine Translation CN102349473 filed with IDS, filed 2012, translated Sep. 27, 2023.*
McMeniman, C.J., et al., "Stable Introduction of a Life-Shortening Wolbachia Infection into the Mosquito *Aedes aegypti*," Supplemental Information, Science, 323: 1-12 (2009).
Walker, T., et al., "The wMel Wolbachia strain blocks dengue and invades caged Aedes aegypti populations," Nature, 476: 450-455 (2011).
McMeniman, C.J., et al., "Stable Introduction of a Life-Shortening Wolbachia Infection into the Mosquito *Aedes aegypti*," Science, 323: 141-144 (2009).
McMeniman, C.J., et al., "Host Adaptation of a Wolbachia Strain after Long-Term Serial Passage in Mosquito Cell Lines," Applied and Environmental Microbiology, 74(22): 6963-6969 (2008).
Parihar, K., et al., "A patent review on strategies for biological control of mosquito vector," World Journal of Microbiology and Biotechnology, 36(187): 1-23 (2020).
Xi, Z., et al., "Wolbachia Establishment and Invasion in an Aedes aegypti Laboratory Population," Science, 310: 326-328 (2005).
Dobson, S., et al., "Fitness advantage and cytoplasmic incompatibility in Wolbachia single- and superinfected Aedes albopictus, " Heredity, 93: 135-142 (2004).
Dobson, S.L., et al., "Mutualistic Wolbachia Infection in Aedes albopictus: Accelerating Cytoplasmic Drive," Genetics, 160: 1087-1094 (2002).
Xi, Z., and Dobson, S.L., "Characterization of Wolbachia Transfection Efficiency by Using Microinjection of Embryonic Cytoplasm and Embryo Homogenate," Applied and Environmental Microbiology, 71(6): 3199-3204 (2005).
Xi, Z., et al., "Generation of a novel Wolbachia infection in *Aedes albopictus* (Asian tiger mosquito) via embryonic microinjection," Insect Biochemistry and Molecular Biology, 35: 903-910 (2005).
Xi, Z., et al., "Interspecific transfer of Wolbachia into the mosquito disease vector Aedes albopictus," Proc. R. Soc. B, 273: 1317-1322 (2006).
Zabalou, S., et al., "Wolbachia-induced cytoplasmic incompatibility as a means for insect pest population control," PNAS, 101(42): 15042-15045 (2004).
Xi, Z., et al., Poster presented at the XXII International Congress of Entomology in Brisbane Queensland Australia entitled "Intraspecific Transfer of Wolbachia in Mosquitoes by Microinjection," (Aug. 15-21, 2004).
Xi, Z., Dissertation entitled "Generation of novel symbiosis in mosquitoes via embryo microinjection and characterization of the Wolbachia/host interaction," (2005).
International Search Report from corresponding PCT Application No. PCT/US2022/043275 dated Jan. 6, 2023.
Written Opinion from corresponding PCT Application No. PCT/US2022/043275 dated Jan. 6, 2023.

* cited by examiner

*Primary Examiner* — Valerie E Bertoglio

(74) *Attorney, Agent, or Firm* — Harness, Dickey & Pierce, PLC

(57) ABSTRACT

Methods of infecting a mosquito with *Wolbachia* and controlling a mosquito population with the *Wolbachia*-infected mosquito are provided herein. The method includes microinjecting a suspension including *Wolbachia* cells and buffer into a target mosquito embryo to produce a *Wolbachia*-infected $G_0$ female. The suspension including *Wolbachia* cells and buffer is obtained by homogenizing a donor insect embryo, tissue, and/or whole body infected with *Wolbachia* to form a homogenate and the *Wolbachia* cells are separated from the homogenate.

17 Claims, 7 Drawing Sheets

```
┌─────────────────────────────────────┐
│ Homogenize Wolbachia-infected       │
│ embryos, tissues, whole body and/or │
│ cell line from donor insect in a buffer │
└─────────────────────────────────────┘
         20
                    │
                    ▼
┌─────────────────────────────────────┐
│ Separate Wolbachia cells from       │
│ homogenate in debris removal step   │
└─────────────────────────────────────┘
      30
                    │
                    ▼
┌─────────────────────────────────────┐
│ Separate Wolbachia cells from       │
│ homogenate in Wolbachia             │
│ concentration step                  │
└─────────────────────────────────────┘
     40
                    │
                    ▼
┌─────────────────────────────────────┐
│ Inject a suspension including       │
│ Wolbachia cells and buffer into a target │
│ mosquito embryo                     │
└─────────────────────────────────────┘
    50
                    │
                    ▼
┌─────────────────────────────────────┐
│ Incubate injected embryos           │
└─────────────────────────────────────┘
    60
                    │
                    ▼
┌─────────────────────────────────────┐
│ Screen and establish infection lines. │
└─────────────────────────────────────┘
    70
```

```
┌─────────────────────────────────┐
│ Homogenize Wolbachia-infected   │
│ embryos, tissues, whole body    │
│ and/or cell line from donor     │
│ insect in a buffer              │
└─────────────────────────────────┘
         20
              ↓
┌─────────────────────────────────┐
│ Separate Wolbachia cells from   │
│ homogenate in debris removal    │
│ step                            │
└─────────────────────────────────┘
         30
              ↓
┌─────────────────────────────────┐
│ Separate Wolbachia cells from   │
│ homogenate in Wolbachia         │
│ concentration step              │
└─────────────────────────────────┘
         40
              ↓
┌─────────────────────────────────┐
│ Separate Wolbachia cells from   │
│ homogenate in another debris    │
│ removal step                    │
└─────────────────────────────────┘
         45
              ↓
┌─────────────────────────────────┐
│ Inject a suspension including   │
│ Wolbachia cells and buffer into │
│ a target mosquito embryo        │
└─────────────────────────────────┘
         50
              ↓
┌─────────────────────────────────┐
│ Incubate injected embryos       │
└─────────────────────────────────┘
         60
              ↓
┌─────────────────────────────────┐
│ Screen and establish infection  │
│ lines.                          │
└─────────────────────────────────┘
         70
```

HOMOGENIZATION METHOD OF INFECTING A MOSQUITO WITH WOLBACHIA

CROSS-REFERENCE TO RELATED APPLICATION

This patent application claims the benefit of U.S. Provisional Patent Application No. 63/398,259 filed on 16 Aug. 2022, the entire contents of which are herein incorporated by reference.

FIELD

The present disclosure relates to methods for infecting a mosquito with a *Wolbachia* infection derived from a homogenized donor insect embryo, tissue, whole body, and/or cell line and methods for controlling a mosquito population.

BACKGROUND

Mosquitos are capable of spreading many deadly diseases to animals and humans by serving as a vector for various pathogens. Examples of mosquito-borne diseases include malaria, dengue and dengue haemorrhagic fever, West Nile, Zika, chikungunya, Yellow Fever, Japanese Encephalitis, human filariasis, and dog heartworm. Almost 700 million people contract a mosquito-borne illness every year resulting in greater than one million deaths. Malaria and other vector-borne diseases are increasing in the world for a variety of reasons, including vector resistance to pesticides, parasite resistance to drugs, increased global travel, climatic changes, etc. Further, many of these mosquito-borne diseases lack a vaccine and/or treatment. Thus, mosquito vectors of disease constitute a major threat to human and animal health.

One method of proposed vector control is use of *Wolbachia* infections to affect harmful insect populations. *Wolbachia* is a genus of obligate, intracellular, maternally inherited bacteria that can infect various insect species. *Wolbachia* infections induce a number of reproductive abnormalities in insects, such as cytoplasmic incompatibility (CI), parthenogenesis, feminization, and male killing. CI occurs in matings between individuals that differ in their *Wolbachia* infection type resulting in karyogamy failure and early embryo death. This ability of *Wolbachia* to induce CI in its host has led to its proposal as a strategy for controlling harmful insect populations, such as via population replacement and population suppression. For example, a *Wolbachia*-infected line of mosquitos can be mass produced and the infected males could be repeatedly released into a mosquito disease vector population, which can then result in eventual suppression of the mosquito population by disrupting the reproductive cycle of the mosquito population. U.S. Pat. No. 7,868,222 reports a method of transinfecting mosquitos with embryonic cytoplasm from a *Wolbachia*-infected donor. Although transfer of embryonic cytoplasm may be considered a more direct route of transinfection, alternative methods of transinfection, for example, using homogenized embryos from a donor insect, are needed. While Xi, Z. et al. (2005) *Appl. Environ. Microbiol.*, 71(6): 3199-3204 reports transinfection of *Drosophila* (fruit fly) with *Wolbachia*-infected embryo cytoplasm and embryo homogenate from a donor fruit fly, further methods are needed for transinfecting a mosquito with *Wolbachia* derived from *Wolbachia*-infected homogenate.

SUMMARY OF THE INVENTION

This section provides a general summary of the disclosure and is not a comprehensive disclosure of its full scope or all of its features.

Provided herein are methods of infecting a mosquito with *Wolbachia*. The method includes microinjecting a suspension including *Wolbachia* cells and buffer into a target mosquito embryo to produce a *Wolbachia*-infected $G_0$ female.

The suspension including *Wolbachia* cells and buffer may be obtained by homogenizing a donor insect embryo, tissue, whole body, and/or cell line infected with *Wolbachia* to form a homogenate and separating the *Wolbachia* cells from the homogenate.

The suspension may contain no detectable amount of cytoplasm from the donor insect embryo, tissue, whole body, and/or cell line infected with *Wolbachia*.

The separating of the *Wolbachia* cells from the homogenate includes (i) a debris removal step, for example, including one or more centrifugation steps, and (ii) a *Wolbachia* concentration step, for example, including one or more centrifugation steps.

The *Wolbachia* concentration step may be performed at a speed of greater than or equal to about 10,000×g for greater than 15 minutes and greater than 4° C.

The *Wolbachia* concentration step may be performed at a speed greater than 12,000×g.

The method may not include a cell lysis step.

The buffer may include sucrose-phosphate-glutamate (SPG) buffer, preferably with about 1% BSA.

The amount of *Wolbachia* cells in the suspension may be from about $2 \times 10^3$ *Wolbachia* surface protein (wsp)/µl to about $1 \times 10^7$ wsp/µl, preferably about $2 \times 10^5$ wsp/µl to about $1 \times 10^6$ wsp/µl.

The target mosquito embryo may be from *Aedes*, *Culex*, or *Anopheles* genera. For example, the target mosquito embryo may be from the *Aedes* genera and may be a species comprising *Aedes albopictus*, *Aedes aegypti* or *Aedes polynesiensis*. Alternatively, the target mosquito embryo may be from the *Anopheles* genus and is a species comprising *Anopheles stephensi*, *Anopheles gambiae*, or *Anopheles arabiensis*. Alternatively, the target mosquito embryo is from the *Culex* genus and is a species comprising *Culex quinquefasciatus*, *Culex pipiens*, or *Culex tarsalis*.

The donor insect embryo, tissue, and/or whole body may be from a mosquito or fruit fly.

The donor insect embryo, tissue, whole body, and/or cell line may be from a mosquito, such as from *Aedes*, *Culex*, or *Anopheles* genera. For example, the donor mosquito embryo, tissue, whole body, and/or cell line may be from the *Aedes* genera and may be a species comprising *Aedes albopictus*, *Aedes aegypti* or *Aedes polynesiensis*. Alternatively, the donor mosquito embryo, tissue, whole body, and/or cell line may be from the *Culex* genera, and may be a species comprising *Culex quinquefasciatus*, *Culex pipiens*, or *Culex pipiens molestus*

The donor insect embryo, tissue, whole body, and/or cell line may be from a fruit fly, such as from *Drosophila* genus. For example, donor insect embryo, tissue, whole body, and/or cell line may be a species comprising *Drosophila melanogaster*, *Drosophila simulans*, or *Drosophila arawakana*.

The donor insect embryo, tissue, whole body, and/or cell line and the target insect embryo may be from different general and/or species. For example, the donor mosquito embryo, tissue, whole body, and/or the cell line may be from

*Aedes albopictus*, and the target mosquito embryo may be from *Aedes aegypti* or *Anopheles stephensi*.

The method may further include mating the *Wolbachia*-infected $G_0$ female mosquito, a *Wolbachia*-infected $G_1$ female mosquito, and/or a *Wolbachia*-infected $G_2$ female mosquito with an uninfected male mosquito. The mating may transmit *Wolbachia* to their offspring with about 100% efficiency.

In another embodiment, a method of controlling a mosquito population is provided. The method includes releasing a mosquito into an environment, wherein the mosquito is infected with *Wolbachia* by a method as described herein.

Other embodiments, including particular aspects of the embodiments summarized above, will be evident from the detailed description that follows.

BRIEF DESCRIPTION OF THE DRAWINGS

The drawings described herein are for illustrative purposes only of selected embodiments and not all possible implementations and are not intended to limit the scope of the present disclosure.

FIG. 1 illustrates a schematic of a method of infecting a mosquito with *Wolbachia* according to the present disclosure.

FIG. 2 illustrates a schematic of another method of infecting a mosquito with *Wolbachia* according to the present disclosure.

FIG. 5A shows living *Wolbachia*. FIG. 5B shows dead *Wolbachia* and FIG. 5C is negative control (SPG buffer).

FIG. 6A is individuals ($G_0$) developed from survived embryos after microinjection. FIG. 6B is the offspring ($G_1$) derived from *Wolbachia*-infected $G_0$ females. FIG. 6C is the offspring ($G_2$) derived from *Wolbachia*-infected $G_1$ parent. A 100% maternal transmission was observed in $G_1$ and $G_1$ of the transinfected line.

Corresponding reference numerals indicate corresponding parts throughout the several views of the drawings.

DETAILED DESCRIPTION

Figure 3:
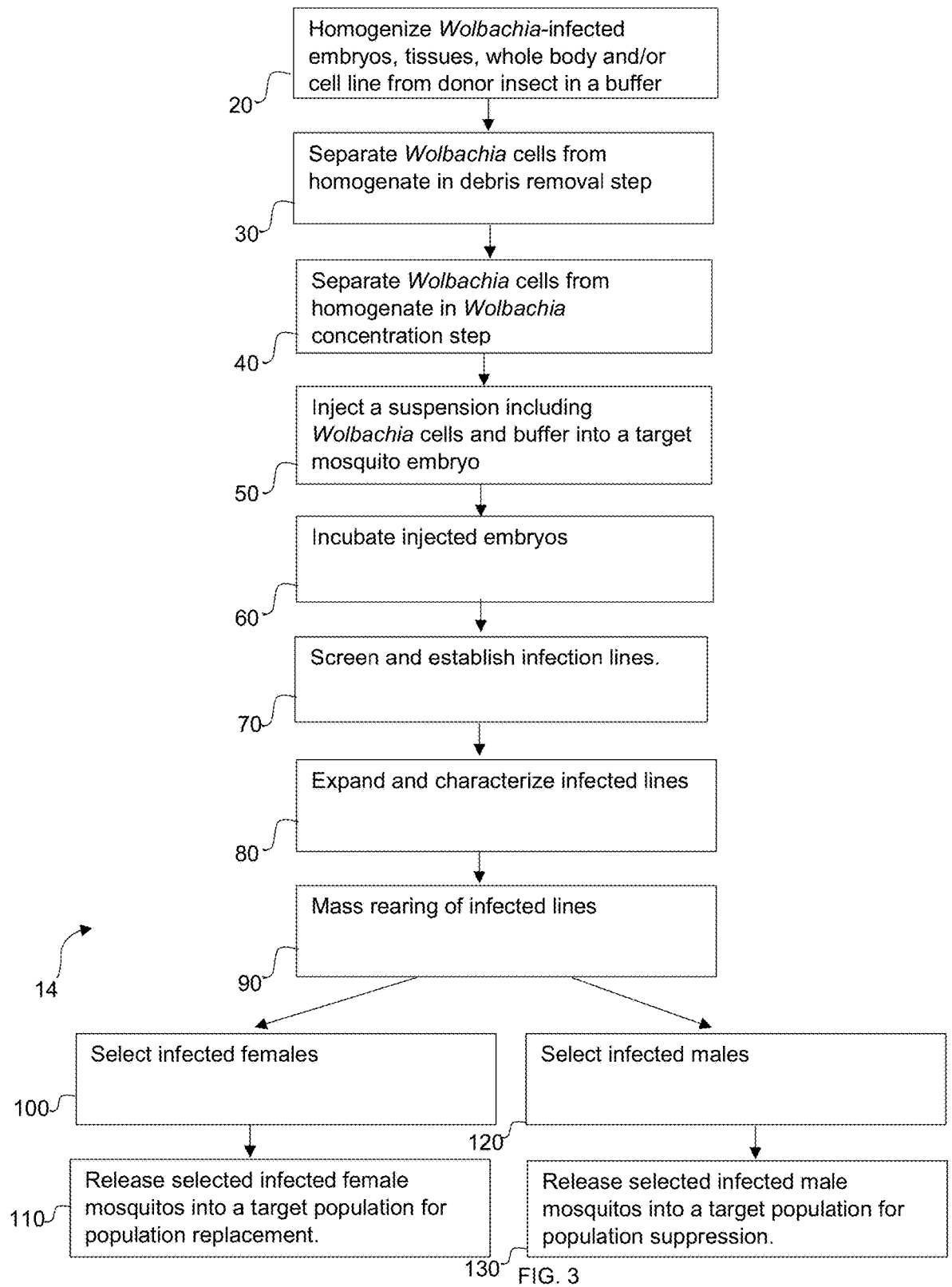
FIG. 3 illustrates a schematic of another method of infecting a mosquito with *Wolbachia* according to the present disclosure.

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term "comprising," is to be understood as a non-restrictive term used to describe and claim various embodiments set forth herein, in certain aspects, the term may alternatively be understood to instead be a more limiting and restrictive term, such as "consisting of" or "consisting essentially of." Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of "consisting of," the alternative embodiment excludes any additional compositions, materials, components, elements, features, integers, operations, and/or process steps, while in the case of "consisting essentially of," any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Any method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

Although the terms first, second, third, etc. may be used herein to describe various steps, elements, components, regions, layers and/or sections, these steps, elements, components, regions, layers and/or sections should not be limited by these terms, unless otherwise indicated. These terms may be only used to distinguish one step, element, component, region, layer or section from another step, element, component, region, layer or section. Terms such as "first," "second," and other numerical terms when used herein do not imply a sequence or order unless clearly indicated by the context. Thus, a first step, element, component, region, layer or section discussed below could be termed a second step, element, component, region, layer or section without departing from the teachings of the example embodiments.

Spatially or temporally relative terms, such as "before," "after," "inner," "outer," "beneath," "below," "lower," "above," "upper," and the like, may be used herein for ease of description to describe one element or feature's relationship to another element(s) or feature(s) as illustrated in the figures. Spatially or temporally relative terms may be intended to encompass different orientations of the device or system in use or operation in addition to the orientation depicted in the figures.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. For example, "about" may comprise a variation of less than or equal to 5%, optionally less than or equal to 4%, optionally less than or equal to 3%, optionally less than or equal to 2%, optionally less than or equal to 1%, optionally less than or equal to 0.5%, and in certain aspects, optionally less than or equal to 0.1%.

In addition, disclosure of ranges includes disclosure of all values and further divided ranges within the entire range, including endpoints and sub-ranges given for the ranges.

Example embodiments will now be described more fully with reference to the accompanying figures.

Methods for infecting (also referred to as "transfecting" or "transinfecting") a mosquito with *Wolbachia* are provided herein. The methods described herein may be used for the suppression, replacement, and/or elimination of mosquito populations due to the ability of *Wolbachia* to induce various reproductive abnormalities in its host, for example, inducing CI in its host. Instead of using *Wolbachia* derived from embryonic cytoplasm from a *Wolbachia*-infected donor insect for transinfection of a mosquito, the methods described herein may use a homogenized embryo, tissue, whole body, and/or cell line from a *Wolbachia*-infected donor insect. While the transfer of embryonic cytoplasm may be considered a more direct route for transinfection, the use of homogenized embryos, tissue, whole body, and/or cell line can be required for technical reasons, such as the physiology of donor embryos. For example, purification of *Wolbachia* following embryo homogenization can reduce complications associated with microinjection of molecules and organelles from donor tissue that can be detrimental to a distantly related recipient host. The use of homogenized tissue can also allow for the simultaneous transfer of multiple *Wolbachia* strains by combining different insect tissues. It will further enable transfer of engineered *Wolbachia* from a cell line to a target insect for application. Additionally, *Wolbachia* enrichment from embryo homogenate can be used to facilitate transinfections from small or weakly infected donor insects.

Referring to FIG. 1, a method 10 for infecting a mosquito with *Wolbachia* is provided. At step 20, *Wolbachia*-infected embryo(s), tissues(s), whole body, and/or a cell line from a donor insect are homogenized with a buffer. In any embodiment, *Wolbachia*-infected embryo(s), tissues(s), and/or whole body from a donor insect may be homogenized with a buffer. If embryo is used for homogenization, the amount of donor insect embryos, depending on the donor insect, that may be homogenized can range from greater than or equal to 200 embryos, greater than or equal to 400 embryos, greater than or equal to 600 embryos, greater than or equal to 800 embryos, greater than or equal to 1000 embryos, greater than or equal to 1200 embryos, greater than or equal to 1400 embryos, greater than or equal to 1600 embryos, less than or equal to 3000 embryos, less than or equal to 2800 embryos, less than or equal to 2600 embryos, less than or equal to 2400 embryos, less than or equal to 2200 embryos, less than or equal to 2000 embryos, less than or equal to 1800 embryos, or less than or equal to 1600 embryos; or from 200 to 3000 embryos, 200 to 2000 embryos, 200 to 1200 embryos or 200 to 1000 embryos.

Homogenization may be accomplished by any suitable methods and equipment known in the art, for example, using a tissue grinder. The buffer may include, for example, sucrose-phosphate-glutamate (SPG), phosphate-buffered saline (PBS), Ringer's buffer, and/or Schneider's media. Optionally, the buffer may also include BSA (bovine serum albumin), and/or FBS (fetal bovine serum), for example, in an amount greater than or equal to about 0.5%, greater than or equal to about 1%, greater than or equal to about 2.5%, greater than or equal to about 5%, less than or equal to about 15%, less than or equal to about 12.5%, less than or equal to about 10%, or less than or equal to about 7.5%; or from about 0.5% to about 15%, about 1% to about $1^20.5$%, or about 1% to about 10%. In any embodiment, the buffer may include SPG, optionally with about 1% BSA.

*Wolbachia* strains contemplated herein for infecting a mosquito include a *Wolbachia* strain that naturally infects a donor insect as well as a *Wolbachia* strain that does not naturally infect a donor insect. Examples of *Wolbachia* strains include, but are not limited to, wAlbA, wAlbB, wStri, wAra, wPanCI, wDi, wSan, wHa, wMelPop, wRi, wCon, wMelCS, wInn, wPip, wAu, and wMel. In any embodiment, a *Wolbachia* strain may include wAlbA, wAlbB, or a combination thereof. The donor insect may be any insect capable of being infected by *Wolbachia*. For example, the donor insect may include a mosquito infected with *Wolbachia* or a non-mosquito insect infected with *Wolbachia*, such as a wasp, beetle, ant, termite, a fruit fly, and a butterfly. In various aspects, the donor insect may be a mosquito and/or a fruit fly.

In any embodiment, the cell line may be infected with any of the *Wolbachia* strains described herein. Alternatively, the cell line may include a wAlbA-infected cell line, wAlbB-infected cell line, wStri-infected cell line, wAra-infected cell line, wPanCI-infected cell line, wDi-infected cell line, wSan-infected cell line, wHa-infected cell line, wRi-infected cell line, wCon-infected cell line, wMelCS-infected cell line, wInn-infected cell line, wPip-infected cell line, wAu-infected cell line, or one or more combinations thereof.

In any embodiment, the method further includes separating *Wolbachia* cells from the homogenate, for example, via a debris removal step 30 and a *Wolbachia* concentration step 40. It is contemplated herein that steps 30 and 40 may be accomplished by one or more centrifugation steps, for example, one, two, three, four, or more centrifugation steps. In any embodiment, the debris removal step 30 and *Wolbachia* concentration step 40 are performed at different speeds, for example, the *Wolbachia* concentration step 40 is performed at a higher speed than the debris removal step 30. In any embodiment, the debris removal step 30 may be performed at a speed of greater than or equal to about 300×g, greater than or equal to about 400×g, greater than or equal to about 500×g, greater than or equal to about 600×g, or about 700×g. Additionally or alternatively, the *Wolbachia* concentration step 40 may be performed at a speed of greater than or equal to about 10,000×g, greater than or equal to about 12,000×g, greater than or equal to about 14,000×g, or about 16,000×g, for example, greater than 12,000×g. During the debris removal step 30, centrifugation may be performed for a suitable amount of time (e.g., 1 minute, 2 minutes, 3 minutes, 5 minutes, 10 minutes, etc.) and repeated one or more times (two, three, four times, etc.) in order to remove debris, such as, shells of embryos (or eggshell), insect cuticle, epicuticle, live cells and cell debris, non-dissolved portions of cell mass (cell wall), organelles and other internal cellular components, exoskeletons, tissues, wings, scales, and cytoplasm. The supernatant collected from the debris removal step 30 may undergo further centrifugation during the *Wolbachia* concentration step 40 for a suitable amount of time (e.g., 1 minute, 2 minutes, 3 minutes, 5 minutes, 10 minutes, etc.) and repeated one or more times (two, three, four times, etc.) to form a pellet of *Wolbachia* cells, which may be resuspended in a buffer as described herein (e.g., SPG with 1% BSA). In an alternative embodiment, as referenced in FIG. 2, following the *Wolbachia* concentration step 40, another or second debris removal step 45 (similar to debris removal step 30) may be performed on the suspension formed from the *Wolbachia* concentration step 40 in a method 12. In any embodiment, the debris removal step and/or the *Wolbachia* concentration each may be performed for greater than or equal to 5 minutes, greater than or equal to 10 minutes, greater than or equal to 15 minutes, greater than or equal to 25 minutes, greater than or equal to 30 minutes, greater than or equal to 45 minutes, or for about 60 minutes; or from about 5 minutes to about 60 minutes, about 10 minutes to about 45 minutes, or about 15 minutes to about 30 minutes. Additional or alternatively, the debris removal step and/or the *Wolbachia* concentration each may be performed a temperature of greater than or equal to about 4° C., greater than or equal to about 8° C., greater than or equal to about 10° C., greater than or equal to about 15° C., greater than or equal to about 25° C., or about 30° C.; or from about 4° C. to about 30° C., about 8° C. to about 25° C., or about 10° C. to about 15° C.

In any embodiment, the method may not include a cell lysis step, such as sonication of cells.

Referring back to FIG. 1, the method further includes injecting a suspension including *Wolbachia* cells into a target mosquito embryo at step 50. In various aspects, the suspension includes a buffer as described herein. The amount of *Wolbachia* cells in the suspension may be from greater than or equal to about $2×10^3$ wsp/µl, greater than or equal to about $2×10^4$ wsp/µl, greater than or equal to about $2×10^5$ wsp/µl, less than or equal to about $1×10^8$ wsp/µl, less than or equal to about $1×10^7$ wsp/µl, or less than or equal to about $1×10^6$ wsp/µl; or from about $2×10^3$ wsp/µl to about $1×10^7$ wsp/µl, or about $2×10^5$ wsp/µl to about $1×10^6$ wsp/µl. The suspension may be microinjected into a posterior end or an anterior end of a target mosquito embryo, in particular, the posterior end of the target mosquito embryo. In various aspects, the suspension contains no detectable amount of cytoplasm from the donor insect embryo, tissue, whole body, and/or cell line infected with *Wolbachia*.

In any embodiment, the donor embryo, tissue, whole body, and/or cell line may be a fruit fly from *Drosophila* genus. Exemplary species from the *Drosophila* genus include, but are not limited to *Drosophila melanogaster*, *Drosophila simulans*, and *Drosophila arawakana*.

In any embodiment, the donor mosquito embryo, tissue, whole body, and/or cell line and the target mosquito embryo independently may be from *Aedes*, *Culex*, or *Anopheles* genera. Exemplary species from the *Aedes* genus include, but are not limited to *Aedes aegypti*, *Aedes africanus*, *Aedes albopictus*, *Aedes australis*, *Aedes cinereus*, *Aedes japonicus*, *Aedes polynesiensis*, *Aedes rusticus*, *Aedes taeniorhynchus*, and *Aedes vexans*. Exemplary species from the *Culex* genus include, but are not limited to *Culex annulirostris*, *Culex asteliae*, *Culex axillicola*, *Culex fasciatus*, *Culex fatigans*, *Culex pseudovishnui*, *Culex quinquefasciatus*, *Culex lineata*, *Culex pipiens*, *Culex pipiens molestus*, *Culex modestus*, *Culex molestus*, *Cluex salinarius*, and *Culex tarsalis*. Exemplary species from the *Anopheles* genus include, but are not limited to *Anopheles atroparvus*, *Anopheles albimanus*, *Anopheles arabiensis*, *Anopheles barberi*, *Anopheles bellator*, *Anopheles crucians*, *Anopheles cruzii*, *Anopheles culicifacies*, *Anopheles darlingi*, *Anopheles earlei*, *Anopheles freeborni*, *Anopheles gambiae*, *Anopheles latens*, *Anopheles moucheti*, *Anopheles nili*, *Anopheles stephensi*, *Anopheles sundacius*, and *Anopheles* walker. For example, the donor mosquito and/or the target mosquito embryo may be from the *Aedes* genus and independently may be a species comprising *Aedes albopictus*, *Aedes aegypti* or *Aedes polynesiensis*. In another example, the donor mosquito and/or the target mosquito embryo may be from the *Anopheles* genus and independently may be a species comprising *Anopheles stephensi*, *Anopheles gambiae*, or *Anopheles arabiensis*. In another example, the donor mosquito may be from the *Culex* genus and is a species comprising *Culex quinquefasciatus*, *Culex pipiens*, or *Culex piepiens molestus* and/or the target mosquito embryo may be from the *Culex* genus and is a species comprising *Culex quinquefasciatus*, *Culex pipiens*, or *Culex tarsalis*.

In some embodiments, the donor insect (e.g., mosquito, fruit fly) embryo, tissue, whole body, and/or cell line and the target mosquito embryo are from different species. For example, the donor mosquito embryo, tissue, whole body, and/or the cell line may be from *Aedes albopictus*, and the target mosquito embryo may be from *Aedes aegypti* and *Anopheles stephensi*.

Additionally or alternatively, steps 20, 30, 40, optionally 45, and 50 can be repeated to create super infections, i.e., a mosquito infected with two *Wolbachia* strains, and repeated a second time to produce a triple infection. For example, a target mosquito embryo can be injected with both wAlbA and wAlbB to cause a superinfection and also injected with wPip to cause a triple infection by repeating steps 20, 30, 40, optionally 45, and 50. Alternatively, the donor insect may have a superinfection, or multiple *Wolbachia* strains from different donor insect hosts may be combined into one suspension, so that injection of the suspension of *Wolbachia* cells into the target mosquito embryo results in a superinfection in the recipient mosquito.

At step 60, the embryos are allowed to mature to produce one or more of a *Wolbachia*-infected female ($G_0$ female) or a *Wolbachia*-infected male ($G_0$ male). Additionally, at step 70, the selection and establishment of *Wolbachia* infected lines may be generated. *Wolbachia* infected lines are established by screening females ($G_0$) surviving the microinjection process for *Wolbachia* infection using a PCR assay. For example, in any embodiment, the method may further include mating a *Wolbachia*-infected $G_0$ female mosquito with an uninfected male mosquito to produce a *Wolbachia*-infected $G_1$ female mosquito and/or a *Wolbachia*-infected $G_1$ male mosquito. Lines established from females that are not infected may be discarded. Lines established from females that are infected may be continued by generating sublines and PCR assays as in the preceding generation. For example, mating of offspring of the *Wolbachia*-infected $G_0$ female mosquito may be performed to produce a *Wolbachia*-infected $G_2$ female mosquito and/or a *Wolbachia*-infected $G_2$ male mosquito, a *Wolbachia*-infected $G_3$ female mosquito and/or a *Wolbachia*-infected $G_3$ male mosquito, and so on. This mating may be repeated for subsequent generations, as needed. For example, a *Wolbachia*-infected $G_1$ female mosquito may be mated with an uninfected male mosquito to produce a *Wolbachia*-infected $G_2$ female mosquito and/or a *Wolbachia*-infected $G_2$ male mosquito, and a *Wolbachia*-infected $G_2$ female mosquito may be mated with an uninfected male mosquito to produce a *Wolbachia*-infected $G_3$ female mosquito and/or a *Wolbachia*-infected $G_3$ male mosquito. Mating of the *Wolbachia*-infected female mosquito (e.g., $G_0$, $G_1$, $G_2$, $G_3$) in the methods described herein may advantageously achieve transmission of *Wolbachia* to their offspring with up to and including about 100% efficiency, for example, greater than or equal about 50% efficiency, greater than or equal about 60% efficiency, greater than or equal about 70% efficiency, greater than or equal about 80% efficiency, greater than or equal about 90% efficiency, or greater than or equal about 95% efficiency; or from about 50% to about 100% efficiency, about 70% to about 100% efficiency, about 80% to about 100% efficiency, about 90% to about 100% efficiency, or about 95% to about 100% efficiency.

Referring to FIG. 3, the method may optionally further include a step 80, comprising an expansion and characterization of appropriate lines. Lines that are stably infected with *Wolbachia* can be expanded by continuing to rear all offspring generated by females. As one female can generate several hundred eggs, the line can be expanded to thousands of insects within a few generations. And, at step 90, the expanded and characterized lines may be reared in mass.

Methods of controlling a mosquito population are provided herein as well. With reference to FIG. 3, a method 14, at step 100 includes selecting *Wolbachia*-infected females as infected by the methods described herein, and, at step 110, the selected females are released into the environment of a mosquito population to induce population replacement for reducing disease transmission as some *Wolbachia* strains induce resistance to human pathogens, including dengue, Zika and malaria parasite, in mosquitoes.

Additionally or alternatively, the method may further include, at step 120, selecting *Wolbachia*-infected male mosquitoes as infected by the methods described herein, which are then subsequently released or introduced into a population of uninfected or differently infected mosquitoes in the environment at step 130. Infected males are allowed to sterilize females that are either uninfected or infected with different strains of *Wolbachia* thereby suppressing or eliminating a population of mosquitoes in a selected population.

It will be apparent to one of ordinary skill in the art that the present method can be used to replace a population of mosquitoes by using the present method to infect female mosquitoes with one or more *Wolbachia* strains and introducing those infected with *Wolbachia* into a population. As the *Wolbachia* infection spreads into the field population, the infection can drive *Wolbachia*-mediated pathogen blocking traits or serve as a vehicle to carry desired transgenes into the targeted population. For example, spread of *Wolbachia* strain wMel into the *Aedes aegypti* population in the field reduces dengue transmission in Indonesia, Australia, and Brazil. See, e.g., Utarini A. et al. (2021) Efficacy of *Wolbachia*-Infected Mosquito Deployments for the Control of Dengue, *N Engl J Med*, 384:2177-2186; Pinto S B, et al. (2021) Effectiveness of *Wolbachia*-infected mosquito deployments in reducing the incidence of dengue and other *Aedes*-borne diseases in Niteroi, Brazil: A quasi-experimental study, *PLoS Negl Trop Dis* 15:e0009556; Ryan P A, et al. (2020) Establishment of wMel *Wolbachia* in *Aedes aegypti* mosquitoes and reduction of local dengue transmission in Cairns and surrounding locations in northern Queensland, Australia, *Gates Open Res*, 3:1547. In particular, successful field trials have shown that *Wolbachia*-based population replacement has reduced dengue incidence by 77.1% and hospitalization by 86.2% in Indonesia. Utarini A. et al. (2021) Efficacy of *Wolbachia*-Infected Mosquito Deployments for the Control of Dengue. *N Engl J Med*, 384:2177-2186. Alternatively, the *Wolbachia* infection has a direct effect on the mosquito population, which has been repeatedly demonstrated for the reduction of vector populations or disease transmission. See, e.g., Howell P. et al. (2020) Efficient production of male *Wolbachia*-infected *Aedes aegypti* mosquitoes enables large-scale suppression of wild populations, *Nature Biotechnology* 38:482-492; Consortium PWS (2021) *Wolbachia*-mediated sterility suppresses *Aedes aegypti* populations in the urban tropics. medRxiv: https://doi.org/10.1101/2021.06.16.21257922; Beebe N W, et al. (2021) Releasing incompatible males drives strong suppression across populations of wild and *Wolbachia*-carrying *Aedes aegypti* in Australia, *Proc Natl Acad Sci USA*, 118 (41)e2106828118; Zheng, X et al. (2019) Incompatible and sterile insect techniques combined eliminate mosquitoes, *Nature*, 572:56-61; Martin-Park A, et al. (2022) Pilot trial using mass field-releases of sterile males produced with the incompatible and sterile insect techniques as part of integrated *Aedes aegypti* control in Mexico, *PLoS Negl Trop Dis*, 16:e0010324.

The present method may aid in controlling the growing burden of vector-borne disease by population suppression/elimination, in which a natural vector population is reduced or eliminated, thus reducing or eliminating the capacity of the population to transmit disease. The present method also may aid in controlling vector-borne disease by population replacement, in which a natural vector population is replaced by a population with a reduced capacity for disease transmission. An important component of such strategy is the drive system, which serves to spread a desired biological trait into the targeted field population. For example, some *Wolbachia* strains induce pathogen blocking in mosquito, but infections do not naturally occur in some important mosquito vectors, such as *Aedes aegypti*. However, using the present method, stable infections of *Wolbachia* can be established and cause a high rate of Cytoplasmic Incompatibility (CI), and consequently the elimination of egg hatch.

EXAMPLES

Example 1—*Wolbachia*-Transinfected Mosquito Using Homogenized Embryos as Donor

This example demonstrates Ae. *aegypti* lines transinfected with wAlbB at 100% maternal transmission efficiency.
Materials and Methods
Donor Embryo Collection
To determine the optimal number of donor embryos, 100, 300, and 1,000 Ae. *albopictus* embryos were collected for *Wolbachia* extraction.
Embryo Homogenization
Embryos were homogenized in 0.5 ml SPG buffer with 1% BSA using a 2-ml KIMBLE Dounce tissue grinder set (Millipore Sigma) (10-20 strokes with the tight-fitting B-type pestle). The homogenate was then transferred to a 1.5-ml eppendorf tube.

Centrifugation

Figure 4:
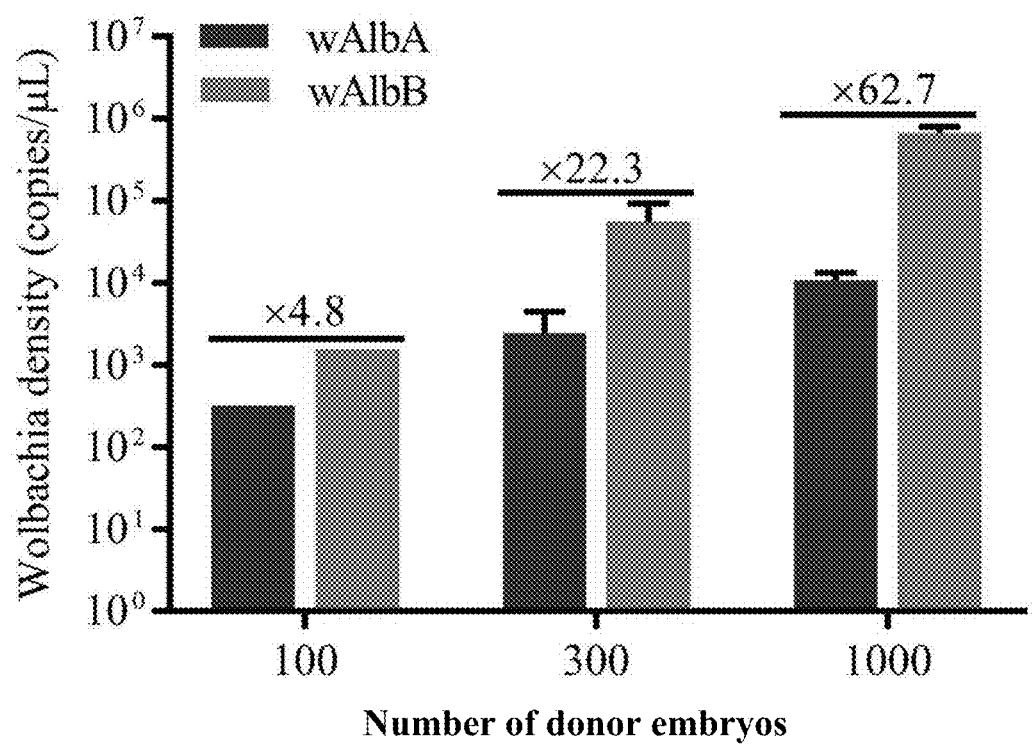
FIG. 4 is a graph illustrating the *Wolbachia* cell density obtained from 100, 300, and 1000 donor mosquito embryos following homogenization and centrifugation.

The resultant homogenate was centrifuged at 400×g for 5 min, repeating twice, to remove large debris, followed by collecting the supernatant and centrifuging at 13,800×g for 10 min to pellet the *Wolbachia* cells. Subsequently, the supernatant was removed, and the pellet was collected and resuspended in ~50 µl SPG with 1% BSA. Debris was cleared from the suspension by centrifuging at 400×g for 3 min. The resultant supernatant, containing the copy number of *Wolbachia*>5×10$^3$ wsp/µl (FIG. 4), was then transferred into a clean tube and used for embryonic microinjection.

Embryonic Microinjection

The supernatant was loaded into a needle using 20-ul Microloader (Eppendorf) and microinjected into the posterior end of early wild-type *Ae. aegypti* AFM embryos, laid within 1-2 hr using an IM300 microinjector (Narishige Scientific) by standard protocol (Xi, Z. et al. (2005a) Generation of a novel *Wolbachia* infection in *Aedes albopictus* (Asian tiger mosquito) via embryonic microinjection. *Insect Biochem Mol Biol*, 35:903-10; Xi, Z. et al. (2005b) *Wolbachia* establishment and invasion in an *Aedes aegypti* laboratory population. *Science*, 310:326-8; Xi, Z. et al. (2006) Interspecific transfer of *Wolbachia* into the mosquito disease vector *Aedes albopictus*. *Proc Biol Sci*, 273:1317-22; Bian, G. et al. (2013) *Wolbachia* invades *Anopheles stephensi* populations and induces refractoriness to *Plasmodium* infection. *Science*, 340:748-51). After injection, the embryos were incubated at 85% RH and 27° C. for 1 h and transferred to wet filter paper. They were then allowed to mature for 4-5 days before being hatched.

*Wolbachia* Viability Assay

Figure 5:
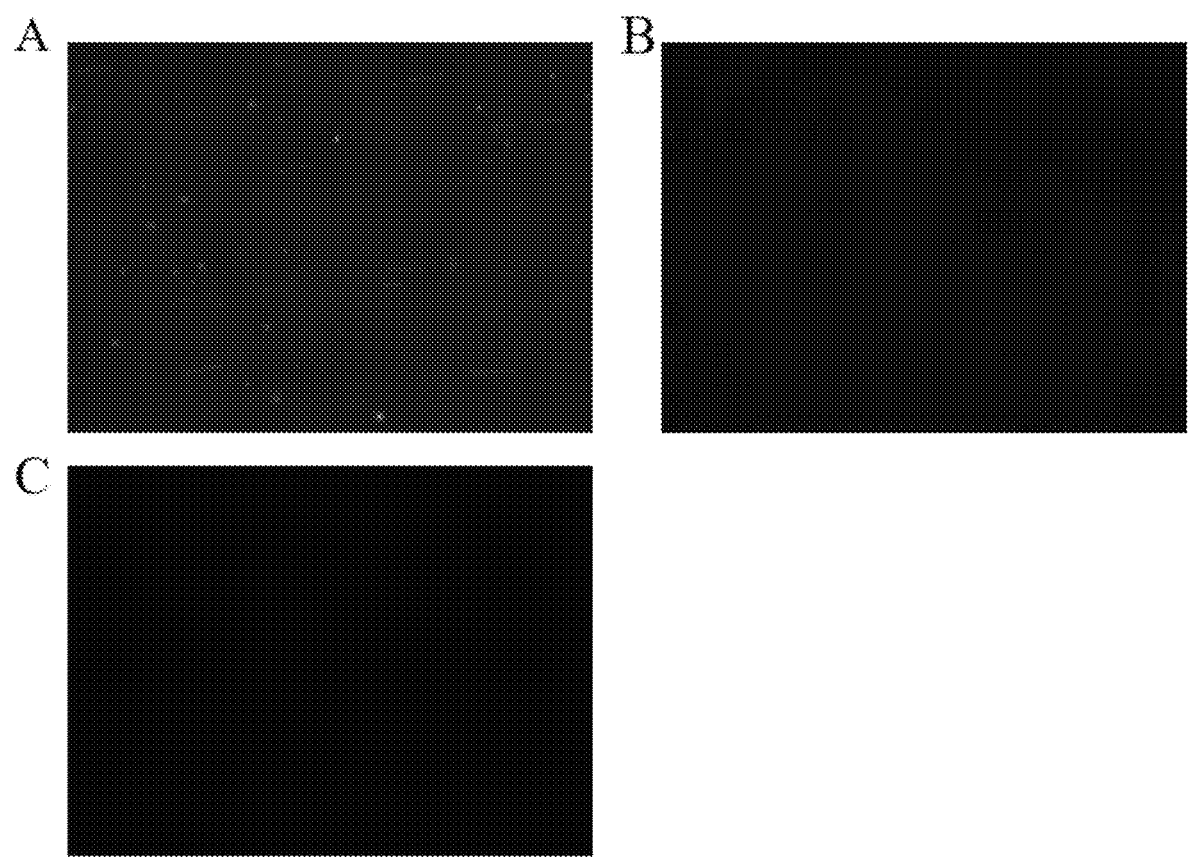
FIGS. 5A-5C are pictures of the viability of *Wolbachia* in the supernatant prepared from embryo homogenate using a Baclight LIVE/DEAD™ bacterial viability kit according to Example 1 herein.

To confirm the isolation of extracellular *Wolbachia* and its viability, a Baclight LIVE/DEAD™ bacterial viability kit was used to differentiate the live and dead bacterial cells in the supernatant, prepared from embryo homogenate, by an Olympus IX71 microscope following manufacturer's instructions (See FIG. 5A-5C) (Krafsure, A M et al. (2020) Phenotypic Response of *Wolbachia pipientis* in a Cell-Free Medium. Microorganisms 8).

PCR Screening for Infection Status

Figure 6:
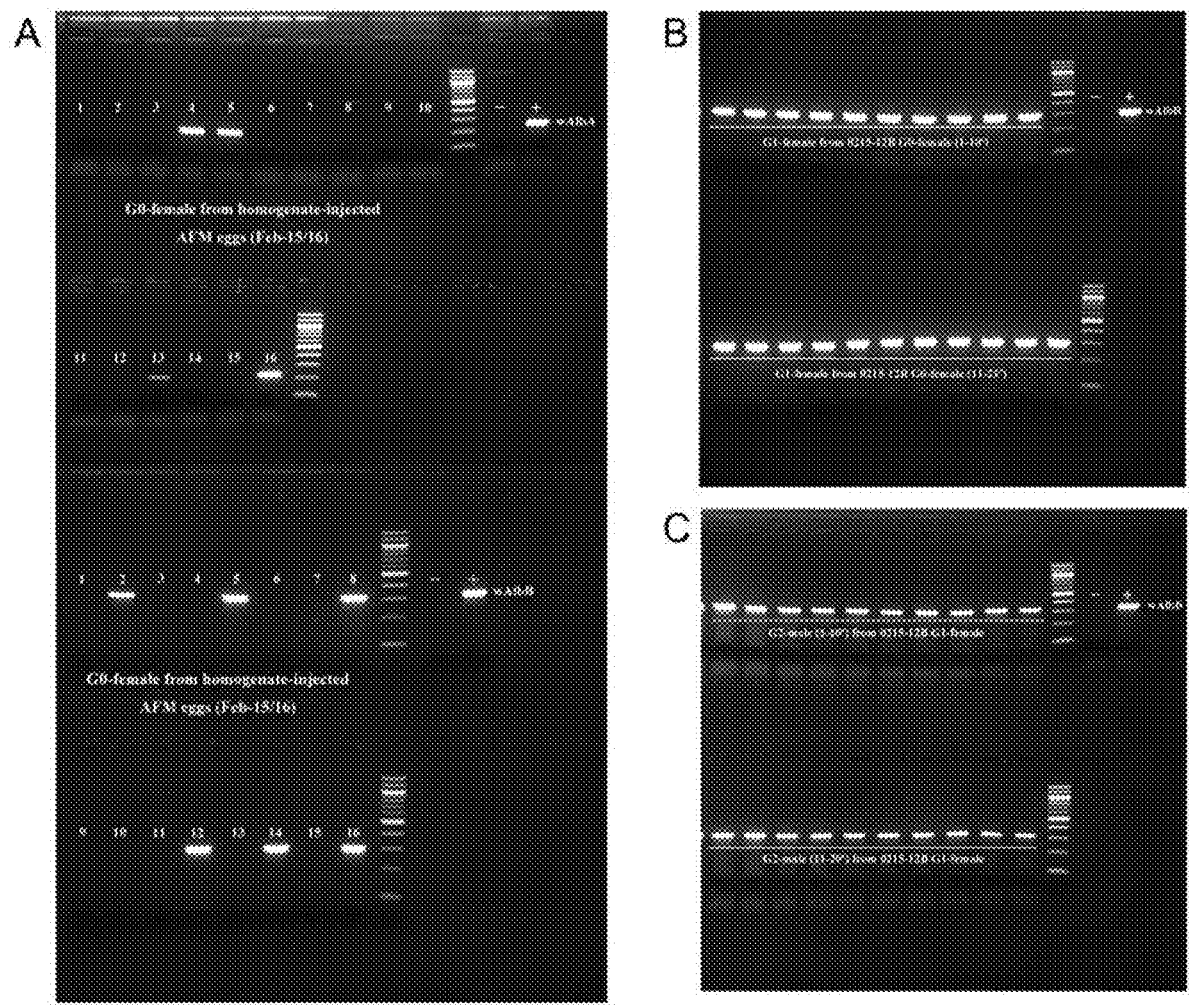
FIGS. 6A-6C demonstrate PCR results to screen for wAlbB infection in $G_0$ females according to Example 1 herein.

Females ($G_0$) developed from the surviving embryos were isolated and mated with wild-type males. After blood-feeding and oviposition, the $G_0$ females were tested for wAlbB infection by PCR using the strain-specific primers described previously (Liang, X. et al. (2020) *Wolbachia* inter-strain competition and inhibition of expression of cytoplasmic incompatibility in mosquito. Front Microbiol: doi: 10.3389/fmicb.2020.01638). $G_1$ females were again crossed with wild-type males, blood-fed, isolated, and allowed to oviposit. The offspring from the wAlbB-positive $G_1$ were selected for the next screen, and this process was repeated until the wAlbB maternal transmission rate reached 100% (See FIG. 6A-6C).

Crossing Assays

Figure 7:
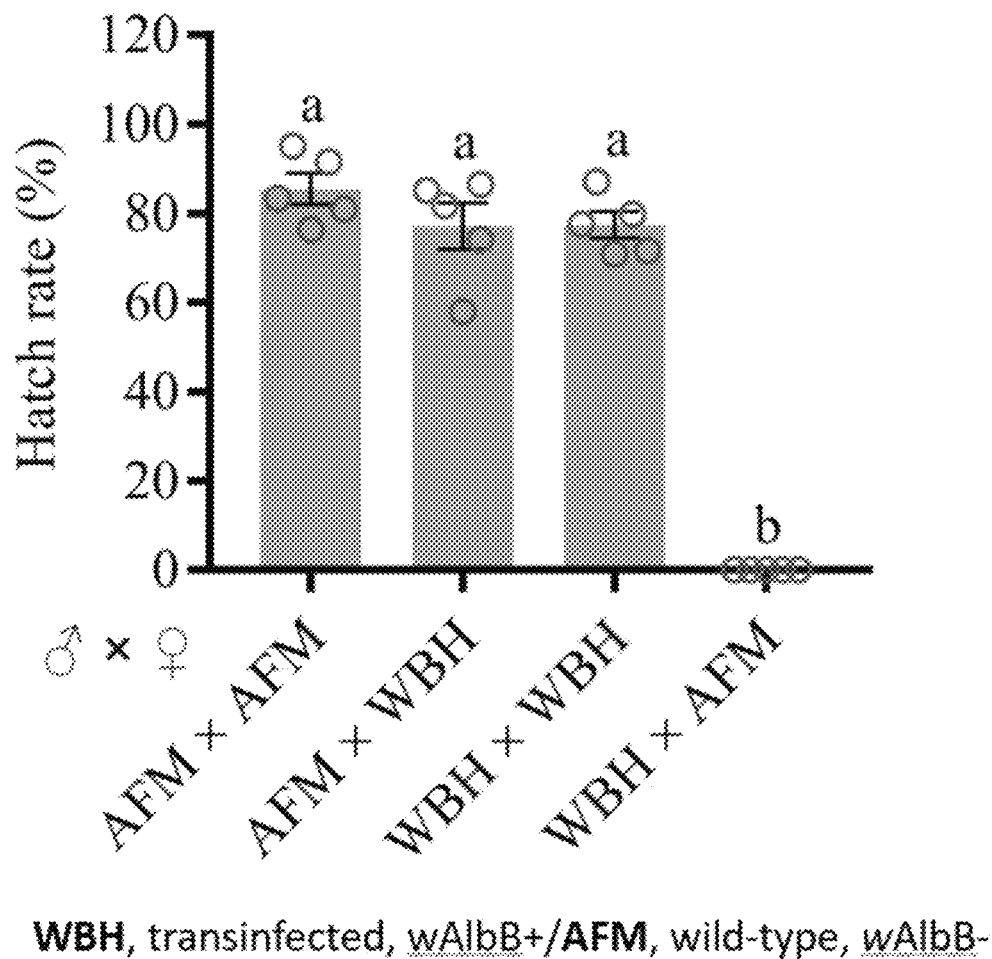
FIG. 7 is a graph illustrating the transinfected *Ae. aegypti* WBH line, generated according to the present disclosure, which induced complete unidirectional cytoplasmic incompatibility in the crosses with the wild-type AFM line. Each cross had five replicates, with ten virgin females mated by ten virgin males.

CI crosses were conducted as previously described (Xi, Z. et al. (2005) *Wolbachia* establishment and invasion in an *Ae. aegypti* laboratory population. Science 310:326-8). Ten virgin males were mated with ten virgin females, with five replicate cages for each cross. A bloodmeal was provided to the females at day 7 post-eclosion. Two days after the bloodmeal, eggs were collected into oviposition cups containing wet filter paper, which were subsequently desiccated for 7 days at 27° C. and 80% relative humidity. Eggs were counted and then hatched in water containing 6% m/v bovine liver powder. Larvae were counted at the L2-L3 stage to record the hatch rate. The results are shown in FIG. 7.

Results

The results from this experiment are summarized in Table 1 below.

TABLE 1

Wolbachia transinfection in *Ae. aegypti* homogenizing embryos as donor

| The number of donor eggs (*Ae. albopictus*) | Number injected | Number hatched | Hatch rate (%) | % Infection frequency (no. positive/no. tested) for: | | | Wolbachia infection for G0-female |
|---|---|---|---|---|---|---|---|
| | | | | G0-male | G0-female | G1 isofemale | |
| 100 | 173 | 27 | 15.6 | 7.7 (1/13) | 0 (0/8) | | |
| 300 | 155 | 6 | 3.9 | 0 (0/2) | 50.0 (1/2) | 0 (0/8) | wAlbA |
| 300 | 206 | 34 | 16.5 | 9.1 (1/11) | 12.5 (1/8) | 20.0 (2/10) | wAlbB |
| 300 | 210 | 34 | 16.2 | 27.3 (3/11) | 20.0 (1/5) | 0 (0/10) | wAlbB |
| 1000 | 208 | 47 | 22.6 | 50.0 (5/10) | 43.8 (7/16) | 100.0 (21/21) | wAlbB |
| | | | | | | 100.0 (3/3) | wAlbA/wAlbB# |
| | | | | | | 16.7 (2/12) | wAlbA |
| | | | | | | 0.0 (0/16) | wAlbB |
| | | | | | | 0.0 (0/16) | wAlbB |
| | | | | | | 0.0 (0/1) | wAlbB |
| | | | | | | 0.0 (0/1) | wAlbA/wAlbB |

:wAlbA was lost in these three G1-female.

The results indicate 1,000 Ae. *albopictus* embryos provide optimal amount of *Wolbachia* with high success rate in transinfection, while 100 and 300 embryos result in either no or low infection in survived individuals. Specifically, from 208 embryos injected with the supernatant from 1,000 egg homogenate, 50% (5/10) of males and 43.8% (7/16) females ($G_0$) survived from embryonic microinjection were *Wolbachia* positive by PCR assay. Among these seven $G_0$ females, one carried wAlbA, four carried wAlbB and two carried a double infection of wAlbA and wAlbB. After mating and bloodfeeding, one of four wAlbB-infected females and one of two double infected females successfully transmitted wAlbB to their offspring (G$_1$) in 100% efficiency. The wAlbA-infected female also transmitted wAlbA to G$_1$ offspring in 16.7% (2/12) efficiency, followed by a 100% maternal transmission efficiency from G$_1$ to G$_2$. Using the supernatant derived from 300 embryos homogenate, one wAlbB-infected G$_0$ female, which transmitted wAlbB to G$_1$ offspring in 20% (2/10) efficiency was also obtained; afterward, these infected G$_1$ females transmitted wAlbB to G$_2$ and G$_3$ offspring in 100% efficiency. Overall, three *Ae. aegypti* lines transinfected with wAlbB at 100% maternal transmission efficiency were generated. These three lines were then combined into one, referred to as the WBH line. At G$_6$, crosses were set up with the transinfected WBH line and the wild-type AFM line. None of eggs hatched when WBH males mated with AFM females whereas all the other three crosses were compatible with each other, with normal egg hatch rates, confirming that the transinfected line, generated by homogenate technique, induces complete cytoplasmic incompatibility (see FIG. 7).

All publications, patent applications, issued patents and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

What is claimed is:

1. A method of infecting a mosquito with *Wolbachia*, the method comprising:
   microinjecting a suspension comprising *Wolbachia* cells and buffer into a target mosquito embryo to produce a *Wolbachia*-infected G$_0$ female, wherein the suspension comprising *Wolbachia* cells and buffer is obtained by homogenizing 1000 or less donor mosquito embryo infected with *Wolbachia* to form a homogenate; and
   separating the *Wolbachia* cells from the homogenate, wherein a copy number of *Wolbachia* surface protein gene (wsp) in the suspension is about 2×10$^5$ wsp/μl to about 1×10$^6$ wsp/μl; and wherein the suspension contains no detectable amount of cytoplasm from the donor insect embryos infected with *Wolbachia*.

2. The method of claim 1, wherein the separating the *Wolbachia* cells from the homogenate comprises:
   (i) a debris removal step; and
   (ii) a *Wolbachia* concentration step.

3. The method of claim 2, wherein:
   (i) the debris removal step comprises one or more centrifugation steps; and
   (ii) the *Wolbachia* concentration step comprises one or more centrifugation steps.

4. The method of claim 2, wherein the *Wolbachia* concentration step is performed at a speed of greater than or equal to about 10,000×g for greater than 15 minutes and greater than 4° C., or wherein the *Wolbachia* concentration step is performed at a speed of greater than 12,000×g.

5. The method of claim 1, wherein the method does not include a cell lysis step.

6. The method of claim 1, wherein the buffer comprises sucrose-phosphate-glutamate (SPG) buffer.

7. The method of claim 1, wherein the target mosquito embryo is from *Aedes*, *Culex*, or *Anopheles* genera.

8. The method of claim 7, wherein the target mosquito embryo is from the *Aedes* genus and is a species comprising *Aedes albopictus*, *Aedes aegypti* or *Aedes polynesiensis*.

9. The method of claim 7, wherein the target mosquito embryo is from the *Anopheles* genus and is a species comprising *Anopheles stephensi*, *Anopheles gambiae*, or *Anopheles arabiensis*.

10. The method of claim 7, wherein the target mosquito embryo is from the *Culex* genus and is a species comprising *Culex quinquefasciatus*, *Culex pipiens*, or *Culex tarsalis*.

11. The method of claim 1, wherein the donor mosquito embryo is independently from *Aedes*, *Culex*, or *Anopheles* genera.

12. The method of claim 11, wherein the donor mosquito embryo is from the *Aedes* genus and is a species comprising *Aedes albopictus*, *Aedes aegypti* or *Aedes polynesiensis*.

13. The method of claim 11, wherein the donor mosquito embryo is from *Culex* genus and is a species comprising *Culex quinquefasciatus*, *Culex pipiens*, or *Culex pipiens molestus*.

14. The method of claim 11, wherein the donor mosquito embryo body is from *Aedes albopictus*, and the target mosquito embryo is from *Aedes aegypti* or *Anopheles stephensi*.

15. The method of claim 1, wherein the donor mosquito embryo and the target mosquito embryo are from different genera and/or species.

16. The method of claim 1, further comprising mating the *Wolbachia*-infected G$_0$ female mosquito, a *Wolbachia*-infected G$_1$ female mosquito, and/or a *Wolbachia*-infected G$_2$ female mosquito with an uninfected male mosquito, wherein the mating transmits *Wolbachia* to their offspring with about 100% efficiency.

17. A method of controlling a mosquito population, the method comprising releasing a mosquito into an environment, wherein the mosquito is infected with *Wolbachia* by a method according to claim 1.

* * * * *